Figure 1:
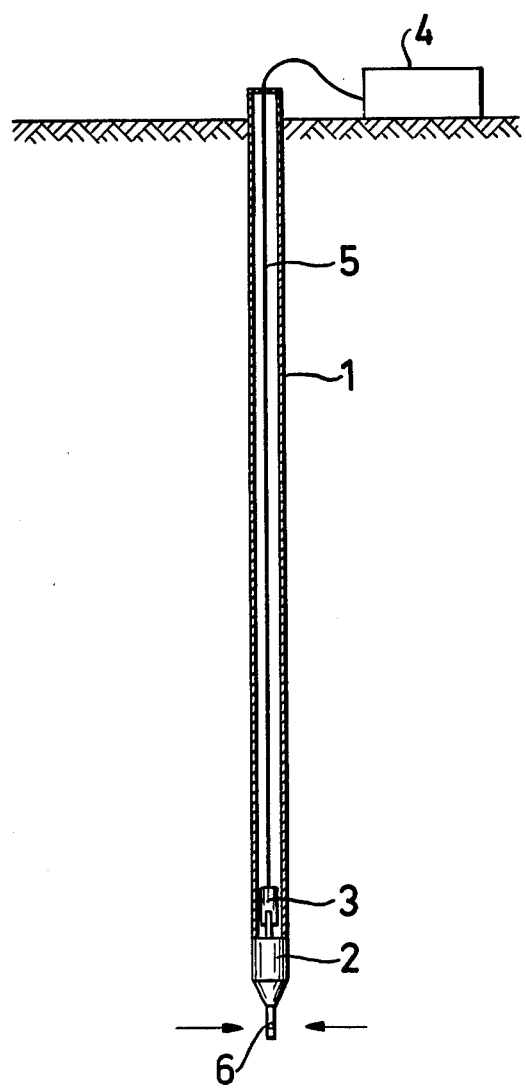

United States Patent [19]

Torstensson

[11] 4,148,212
[45] Apr. 10, 1979

[54] METHOD AND DEVICE FOR DETERMINING THE PORE WATER PRESSURE IN A SOIL

[76] Inventor: Bengt-Arne Torstensson, 34 Hojdvagen, Vallentuna, Sweden

[21] Appl. No.: 844,338

[22] Filed: Oct. 21, 1977

Related U.S. Application Data

[63] Continuation of Ser. No. 691,106, May 28, 1976, abandoned.

[51] Int. Cl.² ............................................. G01M 3/00
[52] U.S. Cl. ...................................................... 73/38
[58] Field of Search ................. 73/38, 64.3, 84, 88 E, 73/73

[56] References Cited

U.S. PATENT DOCUMENTS

| 3,906,781 | 9/1975 | Vlasblom | 73/84 |
| 3,935,745 | 2/1976 | Jonell et al. | 73/704 |

FOREIGN PATENT DOCUMENTS

| 825443 | 12/1937 | France | 73/38 |
| 1236655 | 6/1960 | France | 73/84 |
| 817295 | 7/1959 | United Kingdom | 73/38 |

Primary Examiner—Richard C. Queisser
Assistant Examiner—Joseph W. Roskos
Attorney, Agent, or Firm—Pollock, Vande Sande & Priddy

[57] ABSTRACT

Method of determining the pore water pressure in a soil, which includes installing a water-filled tube bearing a pore pressure sound at its lower end and said pore pressure sound bearing a filter through which the pore pressure in the soil is conveyed; lowering a measuring device down the tube and connecting it to the pore pressure sound; taking a reading which represents the pore pressure in the soil; disconnecting said measuring device from the pore water sound and then taking a reading which represents the water pressure in the tube; and calculating the pore pressure by comparison of the readings for the pore water pressure and the water pressure in the tube. A device for determining the pore water pressure is also provided.

4 Claims, 3 Drawing Figures

METHOD AND DEVICE FOR DETERMINING THE PORE WATER PRESSURE IN A SOIL

This is a continuation, of application Ser. No. 691,106, filed May, 28, 1976, now abandoned.

This invention concerns a method and equipment for determining the pore water pressure in a soil, especially clay.

At the present time there are a large number of methods of determining pore water pressure. A distinction is made between "closed" and "open" measuring systems. In a closed measuring system only a relatively small change in volume is needed for the registration of the pressure; whereas, in an open system a large change in volume is necessary. This invention is primarily intended for the measurement of the pore water pressure in clays, and consists of a closed measuring system.

The biggest disadvantage of the closed measuring systems available today is that the measuring unit is fitted to the pressure sounding tip. This means that the tips are expensive and that it is difficult to make a functional check of the pressure sensing element.

The purpose of the present invention is to offer a method in which the above disadvantages can be avoided. This is done using the following procedure for determining the pore water pressure in a soil:

1. A water-filled tube bearing a pore pressure sound at its lower end is installed at the required level. The pore pressure sound bears a filter through which the pore pressure in the soil is conveyed.
2. A measuring device is lowered down the tube and fitted on to the pore pressure sound.
3. The pore pressure is then allowed to stabilize after which a reading is taken which represents the pore pressure in the soil.
4. The measuring device is disconnected from the pore pressure sound and a reading is taken which represents the water pressure in the tube.
5. The pore pressure is calculated by comparison of the reading for pore water pressure and the water pressure in the tube, using a calibration factor for the measuring device.

Figure 2:
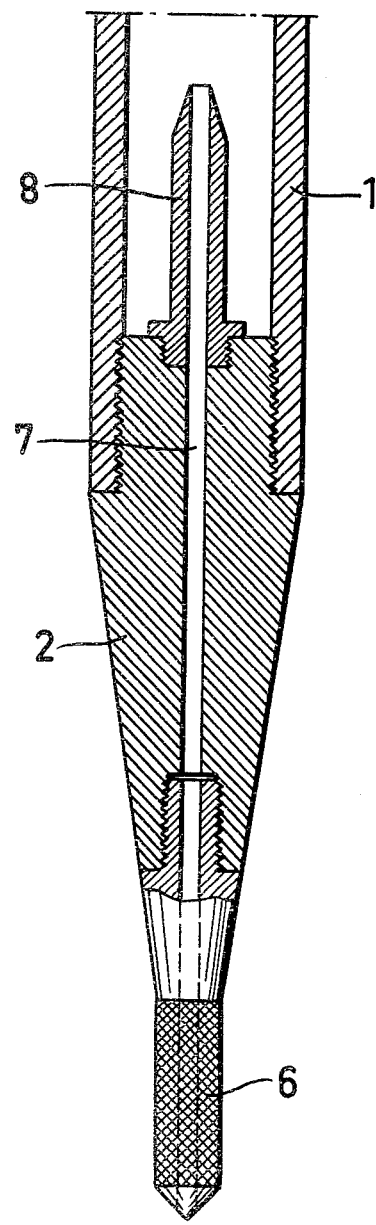
Figure 3:
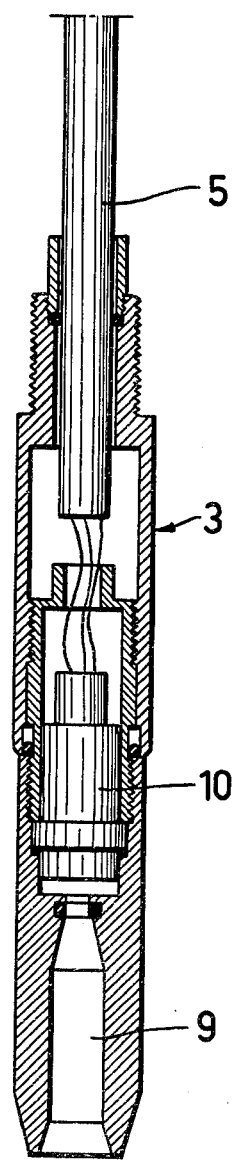

A description of an embodiment of the invention is set forth herein below with reference to the attached drawings; wherein FIG. 1 shows an embodiment of a device according to the invention;

FIG. 2 shows an enlarged cross section through an embodiment of the pore pressure sound; and FIG. 3 shows an enlarged cross section through an embodiment of the measuring device.

The device shown in FIG. 1 includes a water-filled tube 1 which has been installed in the ground. At the lower end of the tube 1 a pore pressure sound 2 has been attached. An embodiment of a pore pressure sound will be shown in greater detail in FIG. 2. The device shown in FIG. 1 also includes a measuring device 3, which has been lowered down the tube 1, and fitted tightly on to a nipple on the pore pressure sound 2. FIG. 3 shows a preferred embodiment of a measuring device on an enlarged scale. As shown in FIG. 1, the measuring device 3 is connected to an electronic read-out unit 4 via an electric cable 5.

FIG. 2 shows a pore pressure sound 2 on an enlarged scale. This is screwed onto the threaded tube 1 at its lower end. The pore pressure sound shown here is very narrow and has a conical form. At the lower end of the sound 2, a filter 6 has been attached. This filter is connected via a duct 7 to a nipple 8. The measuring device 3 shown in FIG. 3 is lowered onto this nipple. At its lower end, this measuring device has a sleeve 9 which fits onto the nipple 8 when the measuring device 3 is lowered. Above the sleeve 9 in the measuring device 3, there is a pressure transducer 10, which is connected to the read-out unit 4 via an electric cable 5.

Pore pressure measurements with the device described above are taken by installing a water-filled tube 1 with a pore pressure sound 2 to the required level. After the disturbance in the soil caused by the penetration of the sound 2 has dissipated, the measuring device 3 is lowered onto the nipple 8 on the pore pressure sound 2. After a short pause while the pore pressure stabilizes, a reading is taken by the read-out unit 4. This reading applies to the pore pressure at the level of the filter 6. After this, the measuring device 2 is disconnected from the nipple 8. A reading which represents the water pressure in the tube 1 is then taken. As this water pressure is known, due to the fact that the length of the tube 1 is known, the pore pressure can be calculated with the help of the following formula:

$$u = p_0 + k(m_1 - m_2) + \Delta h$$

where
- $u$ = pore water pressure
- $p_0$ = water pressure in tube
- $k$ = calibration coefficient for the measurement system
- $m_1$ = reading for pore water pressure
- $m_2$ = reading for water pressure in tube
- $\Delta h$ = distance between pressure transducer and centre of filter.

The readings mentioned above are those supplied by the measuring device 3. These values are then converted by multiplying by the calibration coefficient to give a pressure expressed in a suitable unit, for example in cm water column.

The procedure described above is thus very simple for the people doing the fieldwork. Only two readings are taken: that of the pore water pressure, and that of the water pressure in the tube. For example one is thus not dependent on being able to check possible zero shift of the measurement system.

The equipment is also very simple, and has distinct advantages over previously known equipment. If, for example, the method described above is used for long-time measurements, it is a great advantage that the measuring device is not built into the pore pressure sound, which would make the sounds expensive, as well as making it difficult to subject the pressure sensing element to functional testing.

Another factor which can cause interruption in pore pressure measurements, especially in clay, is corrosion of the pore pressure sound 2. To avoid interruptions of this kind, the pore pressure sound can be made of nylon with a sintered ceramic filter.

The invention is naturally not limited to the method or devices described above. For example, the pore pressure sound can have a cylindrical shape with mainly even thickness instead of the shape shown in FIG. 2. This cylindrical type of pore pressure sound is especially suited to long-time measurements. Also, the measuring device 3 can have a different construction without departure from the scope of the invention. The invention can thus be varied freely within the scope of protection according to the following patent claims.

What is claimed is:

1. Method of determining the pore water pressure in a soil, characterized by the following steps:
    (a) installing at the required level a water-filled tube bearing a pore pressure sound at its lower end and said pore pressure sound bearing a filter through which the pore pressure in the soil is conveyed;
    (b) lowering a measuring device down the tube and connecting said measuring device to said pore pressure sound;
    (c) allowing the pore pressure to stabilize and then taking a reading which represents the pore pressure in the soil;
    (d) disconnecting said measuring device from said pore water sound and then taking a reading which represents the water pressure in the tube; and
    (e) calculating the pore pressure by comparison of the readings for the pore water pressure and the water pressure in the tube, using a calibration factor for the measuring device.

2. The method of claim 1 wherein the readings are taken from an electronic measuring device.

3. The method of claim 1 wherein the measuring device is connected to the pore pressure sound by connecting a sleeve on the measuring device to a nipple on the pore pressure sound.

4. The method of claim 3 wherein the measuring device is connected to the pore pressure sound by connecting a sleeve on the measuring device to a nipple on the pore pressure sound.

* * * * *

UNITED STATES PATENT AND TRADEMARK OFFICE
CERTIFICATE OF CORRECTION

PATENT NO. : 4,148,212
DATED : April 10, 1979
INVENTOR(S) : Bengt-Arne Torstensson It is certified that error appears in the above-identified patent and that said Letters Patent are hereby corrected as shown below:

Please insert the following section:

--Foreign Application Priority Data

May 30, 1975   Sweden      7506203 --.

Signed and Sealed this

Ninth Day of October 1979

[SEAL]

Attest:

RUTH C. MASON
Attesting Officer

LUTRELLE F. PARKER
Acting Commissioner of Patents and Trademarks